US012220185B1

(12) United States Patent
Zak et al.

(10) Patent No.: US 12,220,185 B1
(45) Date of Patent: Feb. 11, 2025

(54) INTERACTIVE VISUALIZATION OF DENTAL IMPLANT POSITION PLANNING

(71) Applicant: Mars Dental AI Ltd., Beit Yitzhak-ShaAr Hefer (IL)

(72) Inventors: Eyal Tsvi Zak, Kibbutz Megiddo (IL); Eyal Toledano, Beit Yitzhak Shaar-Hefer (IL); Ariel Shusterman, Kiriyat Tivon (IL)

(73) Assignee: Mars Dental AI Ltd., Beit Yitzhak-ShaAr Hefer (IL)

( * ) Notice: Subject to any disclaimer, the term of this patent is extended or adjusted under 35 U.S.C. 154(b) by 0 days.

(21) Appl. No.: 18/656,633

(22) Filed: May 7, 2024

(51) Int. Cl.
| | |
|---|---|
| A61B 34/00 | (2016.01) |
| A61B 34/10 | (2016.01) |
| A61B 90/00 | (2016.01) |
| A61C 13/34 | (2006.01) |
| G06T 19/00 | (2011.01) |

(52) U.S. Cl.
CPC .............. A61B 34/25 (2016.02); A61B 34/10 (2016.02); A61B 90/37 (2016.02); A61C 13/34 (2013.01); G06T 19/006 (2013.01); *A61B 2034/102* (2016.02); *A61B 2034/105* (2016.02); *A61B 2090/365* (2016.02); *G06T 2200/24* (2013.01); *G06T 2210/41* (2013.01)

(58) Field of Classification Search
CPC ......... A61B 34/25; A61B 34/10; A61B 90/37; A61B 2034/102; A61B 2034/105; A61B 2090/365; A61C 13/34; G06T 19/006; G06T 2200/24; G06T 2210/41
See application file for complete search history.

(56) References Cited

U.S. PATENT DOCUMENTS

| | | | | |
|---|---|---|---|---|
| 5,688,118 | A * | 11/1997 | Hayka .................. | G09B 23/283 |
| | | | | 433/229 |
| 7,367,801 | B2 * | 5/2008 | Saliger ................... | A61B 90/37 |
| | | | | 433/29 |
| 7,457,443 | B2 | 11/2008 | Persky | |
| 10,064,700 | B2 * | 9/2018 | Fudim ..................... | A61C 1/082 |
| 11,051,914 | B2 * | 7/2021 | Kopelman ........... | A61C 9/0053 |
| 11,357,576 | B2 * | 6/2022 | Jo .......................... | A61B 6/512 |
| 11,399,915 | B2 * | 8/2022 | Colby .................... | A61B 90/11 |

(Continued)

FOREIGN PATENT DOCUMENTS

WO    WO 2022/190105       9/2022

OTHER PUBLICATIONS

Official Action Dated Jul. 12, 2024 From the US Patent and Trademark Office Re. U.S. Appl. No. 18/656,634. (27 Pages).

(Continued)

*Primary Examiner* — Vinh T Lam

(57) ABSTRACT

There is provided an interactive graphical user interface (GUI) for planning positioning of a dental implant in a subject, comprising: presenting, within the GUI, sequential frames of an oral cavity of a subject captured by at least one image sensor during a dental session of the subject, computing a real-world location and/or angle of a real-world tool manipulated by a user, and dynamically updating, within the GUI, an overlay of a virtual angle and/or virtual location of a virtual vector overlaid on the sequential frames corresponding to the real-world location and/or angle of the real-world tool, wherein the virtual vector denotes a location and angle for drilling by a bur of a drill for implanting the dental implant.

22 Claims, 7 Drawing Sheets

(56) References Cited

U.S. PATENT DOCUMENTS

| | | | |
|---|---|---|---|
| 11,510,638 B2 * | 11/2022 | Merritt | A61C 1/082 |
| 11,559,377 B2 * | 1/2023 | Kopelman | G16H 40/60 |
| 11,594,002 B2 * | 2/2023 | Coustaud | G06T 7/0012 |
| 11,684,374 B2 * | 6/2023 | Kang | A61B 17/15 |
| | | | 606/82 |
| 11,727,581 B2 * | 8/2023 | Lang | A61B 90/53 |
| | | | 345/8 |
| 11,730,564 B2 * | 8/2023 | Colby | A61C 3/00 |
| | | | 433/25 |
| 11,751,944 B2 * | 9/2023 | Lang | A61B 90/37 |
| | | | 606/130 |
| 11,771,533 B2 * | 10/2023 | Senn | B29C 33/3835 |
| | | | 264/16 |
| 11,931,114 B2 | 3/2024 | Qian | |
| 11,978,203 B2 * | 5/2024 | Kim | A61C 9/0053 |
| 12,053,247 B1 | 8/2024 | Chiou | |
| 2011/0045432 A1 | 2/2011 | Groscurth et al. | |
| 2013/0172731 A1 | 7/2013 | Gole | |
| 2013/0302752 A1 | 11/2013 | Schneider | |
| 2013/0309628 A1 | 11/2013 | Orth et al. | |
| 2014/0186794 A1 | 7/2014 | Deichmann et al. | |
| 2014/0272773 A1 | 9/2014 | Merritt et al. | |
| 2015/0150655 A1 | 6/2015 | Frank et al. | |
| 2015/0296184 A1 | 10/2015 | Lindenbert et al. | |
| 2016/0135904 A1 | 5/2016 | Daon et al. | |
| 2016/0235481 A1 | 8/2016 | Dorman | |
| 2018/0008355 A1 | 1/2018 | Mozes et al. | |
| 2018/0168781 A1 | 6/2018 | Kopelman et al. | |
| 2019/0038367 A1 | 2/2019 | Ciriello et al. | |
| 2019/0269482 A1 | 9/2019 | Shanjani et al. | |
| 2019/0350680 A1 | 11/2019 | Chekh et al. | |
| 2020/0008877 A1 | 1/2020 | Jo et al. | |
| 2020/0138518 A1 | 5/2020 | Lang | |
| 2021/0161626 A1 | 6/2021 | Kim et al. | |
| 2021/0186454 A1 | 6/2021 | Behzadi et al. | |
| 2021/0192759 A1 | 6/2021 | Lang | |
| 2022/0015875 A1 * | 1/2022 | Palmer | A61C 13/34 |
| 2022/0047278 A1 | 2/2022 | Fitz et al. | |
| 2022/0084267 A1 * | 3/2022 | Ezhov | A61B 6/4085 |
| 2022/0257332 A1 | 8/2022 | Duong | |
| 2022/0287676 A1 | 9/2022 | Steines et al. | |
| 2022/0361992 A1 * | 11/2022 | Ezhov | G06T 19/00 |
| 2023/0252748 A1 * | 8/2023 | Ezhov | A61B 6/4085 |
| 2023/0298272 A1 * | 12/2023 | Ezhov | A61C 9/0053 |
| | | | 345/423 |
| 2023/0414318 A1 * | 12/2023 | Colby | A61B 34/10 |
| 2023/0419631 A1 * | 12/2023 | Ezhov | G16H 50/20 |
| 2024/0041530 A1 * | 2/2024 | Lang | A61B 17/155 |
| 2024/0046490 A1 * | 2/2024 | Lang | A61C 5/40 |
| 2024/0148469 A1 * | 5/2024 | Colby | A61C 1/082 |

OTHER PUBLICATIONS

Notice of Allowance Dated Sep. 30, 2024 from the US Patent and Trademark Office Re. U.S. Appl. No. 18/656,634. (7 Pages).

* cited by examiner

INTERACTIVE VISUALIZATION OF DENTAL IMPLANT POSITION PLANNING

RELATED APPLICATIONS

This application is related to co-filed U.S. Patent Application entitled "INTERACTIVE GUIDANCE OF DENTAL IMPLANT SURGERY", U.S. patent application Ser. No. 18/656,634, filed on May 7, 2024, the contents of which are incorporated herein by reference in their entirety.

This application is also related to International Patent Application No. PCT/IL2022/050274, having Publication No. WO2022/190105, entitled "ENHANCING DENTAL VIDEO TO CT MODEL REGISTRATION AND AUGMENTED REALITY AIDED DENTAL TREATMENT", filed on Mar. 10, 2022, the contents of which are incorporated herein by reference in its entirety.

BACKGROUND

The present invention, in some embodiments thereof, relates to user interfaces and, more specifically, but not exclusively, to a user interface for use during a dental procedure.

User interface technologies have dramatically evolved in recent times and have spread to numerous applications, uses and practices. Among other applications, the use of user interfaces to support dental procedures has also dramatically increased, in particular for more complex dental procedures such as, for example, dental surgery, dental implants and/or the like.

SUMMARY

According to a first aspect, an interactive graphical user interface (GUI) for planning positioning of a dental implant in a subject, comprises: presenting, within the GUI, sequential frames of an oral cavity of a subject captured by at least one image sensor during a dental session of the subject, computing a real-world location and/or angle of a real-world tool manipulated by a user, and dynamically updating, within the GUI, an overlay of a virtual angle and/or virtual location of a virtual vector overlaid on the sequential frames corresponding to the real-world location and/or angle of the real-world tool, wherein the virtual vector denotes a location and angle for drilling by a bur of a drill for implanting the dental implant.

According to a second aspect, a system for presenting an interactive graphical user interface (GUI) for planning positioning of a dental implant in a subject, comprises: at least one processor executing a code for: presenting, within the GUI, sequential frames of an oral cavity of a subject captured by at least one image sensor during a dental session of the subject, computing a real-world location and/or angle of a real-world tool manipulated by a user, and dynamically updating, within the GUI, an overlay of a virtual angle and/or virtual location of a virtual vector overlaid on the sequential frames corresponding to the real-world location and/or angle of the real-world tool, wherein the virtual vector denotes a location and angle for drilling by a bur of a drill for implanting the dental implant.

In a further implementation form of the first and second aspects, the GUI including the sequential frames and overlay are presented within an augmented reality device.

In a further implementation form of the first and second aspects, the real-world tool comprises the drill for inserting the dental implant.

In a further implementation form of the first and second aspects, the virtual angle and/or virtual location of the virtual vector is offset from the real-world location of the real-world tool being manipulated for dynamically updating the virtual vector.

In a further implementation form of the first and second aspects, further comprising: receiving a selection of at least one dental-related anatomical structure of the subject, presenting within the GUI, at least one fused frame depicting a merger of the sequential frames and a segmentation of the at least one dental-related anatomical structure of the subject segmented from a dental 3D imaging model registered to the sequential frames, wherein the overlay of the virtual vector is overlaid on the at least one fused frame, and the virtual vector is depicted with respect to the segmentation of the at least one dental-related anatomical structure.

In a further implementation form of the first and second aspects, the at least one dental-related anatomical structure comprises an internal anatomical structure located below an intraoral surface of the subject.

In a further implementation form of the first and second aspects, further comprising dynamically updating within the GUI, the virtual vector depicted at least partially penetrating the segmentation of the at least one dental-related anatomical structure according to manipulations of the tool by the user.

In a further implementation form of the first and second aspects, further comprising dynamically updating within the GUI, a presentation of distance between the virtual vector and the at least one dental-related anatomical structure.

In a further implementation form of the first and second aspects, further comprising generating an indication within the GUI, indicating whether the virtual vector is within a safe margin and/or poses a risk, according to the distance.

In a further implementation form of the first and second aspects, the at least one dental-related anatomical structure is selected from: roots of teeth, jawbone, and at least one nerve.

In a further implementation form of the first and second aspects, further comprising dynamically adapting within the GUI, a second overlay over the sequential frames of a virtual angle and/or virtual location of a 3D virtual model of a dental implant for implantation along the virtual vector, according to the corresponding physical angle and/or physical location of the tool manipulated by the use.

In a further implementation form of the first and second aspects, further comprising in response to an input from a user, dynamically adapting a size and/or shape and/or type of the dental implant and/or of a dental prosthesis designed to connect to the dental implant.

In a further implementation form of the first and second aspects, further comprising presenting within the GUI, a dental 3D visual model of the subject created based on a visible light spectrum intraoral scan of the subject, the dental 3D visual model presented as a second overlay on the sequential frames according to a registration between the dental 3D visual model, a dental 3D imaging model, and the sequential frames, wherein the virtual vector is overlaid on the dental 3D visual model and the sequential frames according to a corresponding physical angle and/or physical location of the tool manipulated by the user.

In a further implementation form of the first and second aspects, the dental 3D visual model is created by an intraoral scanner capturing images at the visual light spectrum.

In a further implementation form of the first and second aspects, further comprising dynamically updating within the GUI, the virtual vector depicted at least partially penetrating the dental 3D visual model, according to manipulations of the tool by the user.

In a further implementation form of the first and second aspects, further comprising: in response to an input from a user, fixing a location and/or an angle of the virtual vector with respect to the subject, and dynamically updating within the GUI, the overlay indicating the fixed location and/or angle of the virtual vector on subsequent frames, wherein the fixed location and/or angle is independent of the real-world location and/or angle of the real-world tool.

In a further implementation form of the first and second aspects, fixing comprises fixing the location of the virtual vector while dynamically updating the angle of the virtual location according to manipulations of the tool, and fixing the angle with respect to the fixed location of the virtual vector.

In a further implementation form of the first and second aspects, further comprising: presenting within the GUI, a 3D virtual model of the dental implant at a location and angle corresponding to the fixed location and angle.

In a further implementation form of the first and second aspects, further comprising, within the GUI, dynamically adapting the virtual angle and/or virtual location of a second virtual vector presented simultaneously with the positioned 3D virtual model of the dental implant, for planning insertion of a second dental implant with respect to the 3d virtual model of the dental implant.

According to a third aspect, a computer implemented method of generating an interactive user interface for planning positioning of a dental implant in a subject, comprises: receiving a selection of at least one dental-related anatomical structure of the subject, receiving at least one frame of an oral cavity of a subject captured by at least one image sensor during a dental session of the subject, registering the at least one frame to a dental 3D imaging model, accessing a segmentation of the at least one dental-related anatomical structure segmented from the dental 3D imaging model, creating at least one fused frame merging the at least one frame with the segmentation of the at least one dental-related anatomical structure, and dynamically adapting an overlay of a virtual angle and/or a virtual location of a virtual vector overlaid on the at least one fused frame according to a corresponding real-world location and/or angle of a real-world tool manipulated by a user.

In a further implementation form of the third aspect, further comprising: receiving a dental 3D visual model of the subject created based on a visible light spectrum intraoral scan of the subject, registering the dental 3D visual model to the dental 3D imaging model, registering the at least one frame to the dental 3D visual model according to at least one intraoral marker, registering the at least one frame to the dental 3D imaging model according to the registration of the at least one frame to the dental 3D visual model and the registration of the dental 3D visual model to the dental 3D imaging model, creating at least one second fused frame by merging the at least one frame with a corresponding portion of the registered dental 3D visual model, and dynamically adapting a second overlay of the virtual angle and/or the virtual location of the virtual vector overlaid on the at least one second fused frame according to a corresponding physical angle and/or physical location of the tool manipulated by the user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
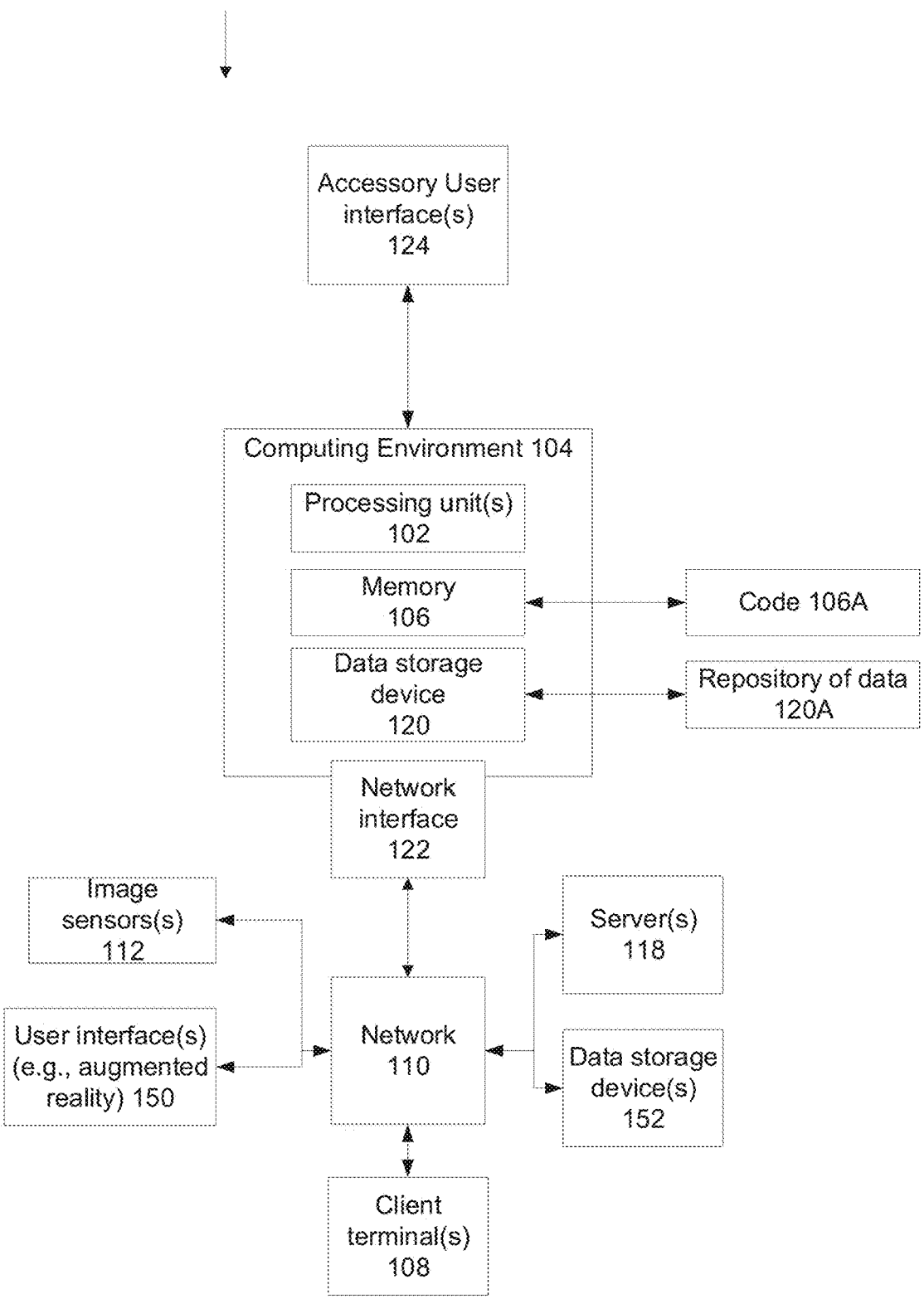
FIG. 1 is a block diagram of a system for generating and/or updating a GUI for planning positioning of a dental implant in a subject, in accordance with some embodiments of the present invention.

The present invention, in some embodiments thereof, relates to user interfaces and, more specifically, but not exclusively, to a user interface for use during a dental procedure.

An aspect of some embodiments of the present invention relates to systems, methods, computing devices, and/or code instructions (stored on a data storage device and executable by one or more processors) for generating and/or updating a user interface, optionally a graphical user interface (GUI) for planning positioning of a dental implant in a subject, for example, for a dental prosthesis such as a crown. The GUI may be presented within an augmented reality (AR) device worn by a user (e.g., dentist), and/or presented on a display such as for viewing by an assistant to the user (e.g., dental assistant). Sequential frames of an oral cavity of a subject are accessed. The sequential frames are captured by one or more image sensors, such as a camera, optionally installed on the AR device. The sequential frames may be captured during a dental session of the subject for insertion of a dental implant. The sequential frames may be presented within the GUI. A processor(s) computes a real-world location and/or a real-world angle of a real-world tool manipulated by a user. The real-world tool may be a drill with a bur used by the user for drilling in the jaw of the subject for insertion of the dental implant. A virtual vector for presentation of the GUI, is defined by a virtual location and/or virtual angle corresponds to the computed real-world location and/or real-world angle, such that manipulations of the tool by the user dynamically update the virtual vector accordingly. The virtual vector indicates a location and angle for drilling by the bur of the drill for implanting the dental implant. An overlay of the virtual angle and/or virtual location of the virtual vector over the sequential frames within the GUI is dynamically updated in response to manipulations by the user and/or in response to changes in pose of the camera(s) (e.g., due to head movements by the user wearing the AR device).

Optionally, one or more other visual elements are presented as overlays over the sequential frames within the GUI, and are dynamically updated. The other visual elements may be presented simultaneously with the virtual vector, optionally intersecting the virtual vector. Examples of other visual elements include: dental-related anatomical structures of the subject (e.g., jaw bone, one or more nerves, roots of teeth), alerts such as distance between the virtual vector and dental-related anatomical structures is below a threshold, 3D virtual model of the dental implant, and a dental 3D visual model.

At least one embodiment described herein addresses the technical problem of providing tools for planning a dental implant procedure (e.g., the dentist), by defining the location and angle to drill in order to insert a dental implant. Performing a surgical procedure without planning and deliberation lead to poor surgical and clinical results and complications. Precise drilling at a specific location and at a specific angle may be important, for example, for optimal placement of the dental implant, minimizing damage to surrounding structures, improving osseointegration, enhancing aesthetic outcomes, reducing risk of implant failure, facilitating prosthetic restoration, and the like.

In some existing approaches, imaging studies such as CT are performed. In many cases a technician or a specialist, and in some cases the surgeon themselves, may visualize the imaging study in a 3D suite or use a dedicated surgical planning software and other tools available to view, visualize and measure. These visualizations and measurements may be used to select the optimal parameters for the surgery. For example, selecting the correct implant size. An implant that is too small will not provide strong enough support for loading the crown. On the other hand, an implant that is too long can hit a nerve or exit the bone envelope. After the implant type, size, location and angulation is selected, and the surgical plan is approved by the surgeon, the surgical plan may be exported to 3D tools to create a fixed surgical guide or to program a dynamic navigation system.

The challenge with the existing approaches is that the workflow requires interactions by a specialist. Moreover, the existing planning approaches takes a lot of time, sometimes up to 3 weeks. Many dentists, especially experienced ones, do not want to spend 30 minutes or one hour on planning an implant that would take them about 7 minutes to place. Rather, these dentists rely on their memory and experience to decide their course of action after viewing the CT image, without really making a CAD plan.

At least one embodiment described herein addresses the aforementioned technical problem, and/or improves upon the aforementioned existing approaches, and/or improves upon the aforementioned technical field, by providing tools for making a surgical plan based on imaging modalities (e.g., CT, MRI, and the like) in order to identify and understand the anatomy and/or select the best clinical approach, and/or select the tools to use, for example implant type, implant size, location for insertion of the implant, and/or angle at which the implant is to be inserted. The plan may take into account the goal of the surgical procedure with respect to the specific personal condition of the patient and/or their anatomy as reflected by the imaging modalities and/or prior examinations.

At least one embodiment described herein addresses the aforementioned technical problem, and/or improves upon the aforementioned existing approaches, and/or improves upon the aforementioned technical field, by providing tools for allowing dentists to generate an accurate surgical plan. The plan may be generated dynamically and/or substantially immediately prior to the surgery, such as in cases that they would otherwise avoid making. The ability to present the plan as an overlay on images depicting the mouth of the subject prior to execution of the surgery can also help visualize the end result. Using prior approaches, using a general 3D tool for planning does not provide alerts on misplacement and/or there are no alerts indicating adversely affected important anatomical landmarks. In contrast, in at least one embodiment described herein, the dentist is provided with alerts, and the source of the alert may be visualized. For example, if the plan is for placing the implant too close to the nerve, the distance may be measured and/or automatically presented. The alert may visually highlight that the distance is too close to the user, enabling the user to react and correct the plan (e.g., immediately and/or quickly), prior to performing the surgery.

At least one embodiment described herein addresses the aforementioned technical problem, and/or improves upon the aforementioned existing approaches, and/or improves upon the aforementioned technical field, by dynamically updating an overlay over a GUI depicting sequential frames of an oral cavity of a subject captured by an image sensor. The overlay depicts a virtual angle and/or a virtual location of a virtual vector that corresponds to a real-world location and/or real-world angle of a real-world tool, optionally a drill having a bur used for drilling into the jaw of the subject for insertion of a dental implant, which may connect to a dental prosthesis. The virtual vector indicates a location and angle for drilling by the bur of the drill for implanting the dental implant. The virtual vector presented on the GUI over the frames of the oral cavity is dynamically updated in response to manipulations of the real-world tool by the user. The GUI enables the user to use the tool to manipulate the virtual vector for planning the location and angle for drilling using the bur of the drill. Other visual elements as described herein may be presented in the GUI and dynamically updated accordingly.

In at least one embodiment described herein, the user (e.g., dentist) may use a hand-piece, such as the dental drill, as a 3D positioning input mechanism (e.g., like a 3D mouse). One potential advantage to this approach is that the user is used to this tool and feels comfortable directing it. Another potential advantage to this approach is that when the user is planning and moving the hand piece, the user is also positioning the implant in a way that is easier for the user to access. The user may actually rehearse a surgical approach to the location and/or angle physically before final placement of the dental implant. The likelihood that the user (e.g., dentist) will place the implant in a location that is not feasible easily to access with the hand piece is reduced or eliminated based on using approaches according to at least one embodiment described herein. In contrast, such situation of infeasible access may occur when planning the surgery offline on a standard 3D application with a mouse that does not have 3D degrees of freedom. Moreover, such standard applications do not take into account the specific physical limitations of the specific patient, the specific dentist, and specific tools used. In contrast, using at least one embodiment described herein to plan the surgery may save a lot of time in the process and/or make it easy for the dentist to use their own tools in designing the surgical plan, in particular without the need to learn and operate complex 3D imaging software on a computer.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
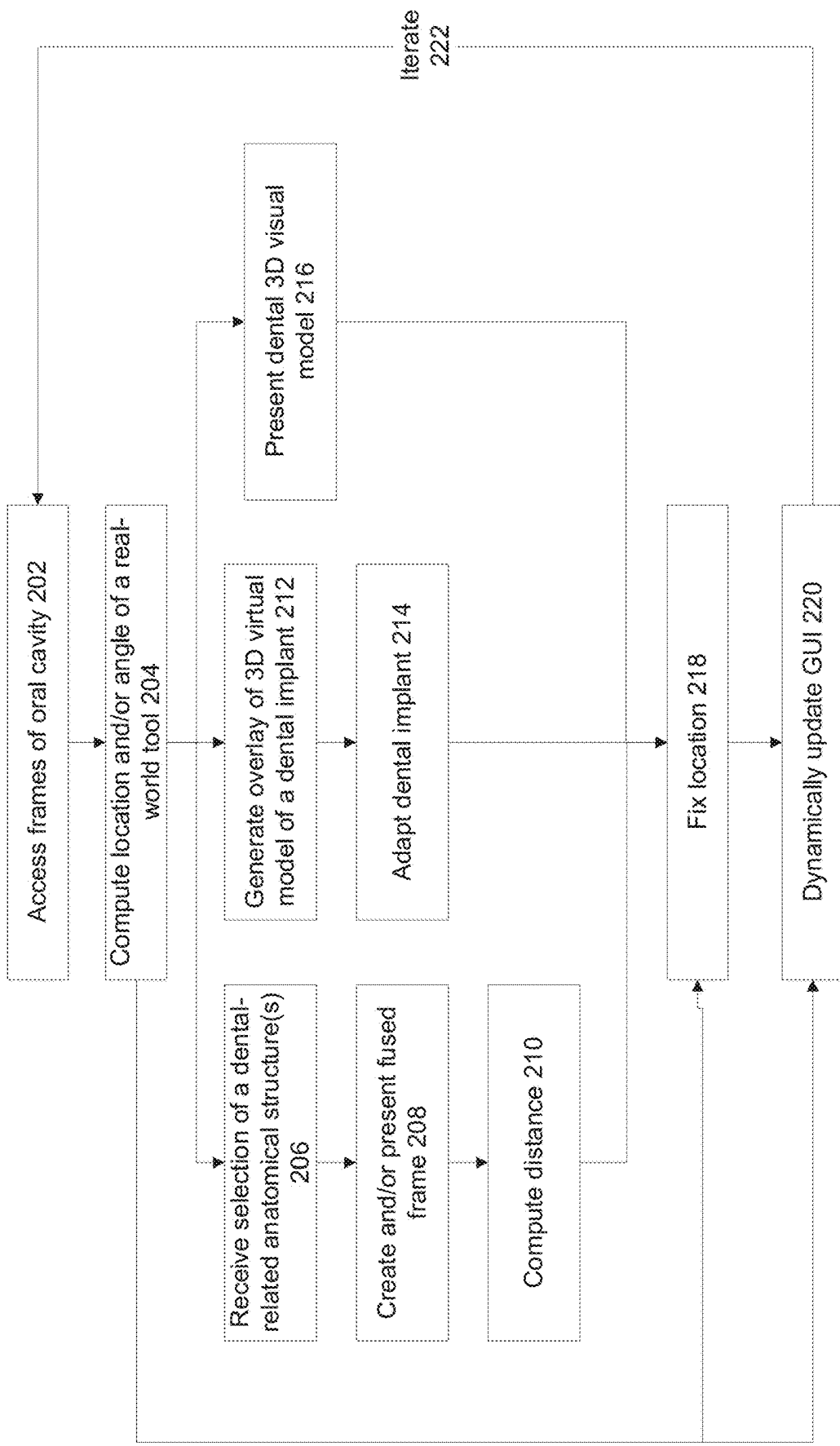
FIG. 2 is a flowchart of a method of generating and/or updating a GUI for planning positioning of a dental implant in a subject, in accordance with some embodiments of the present invention.
Figure 3:
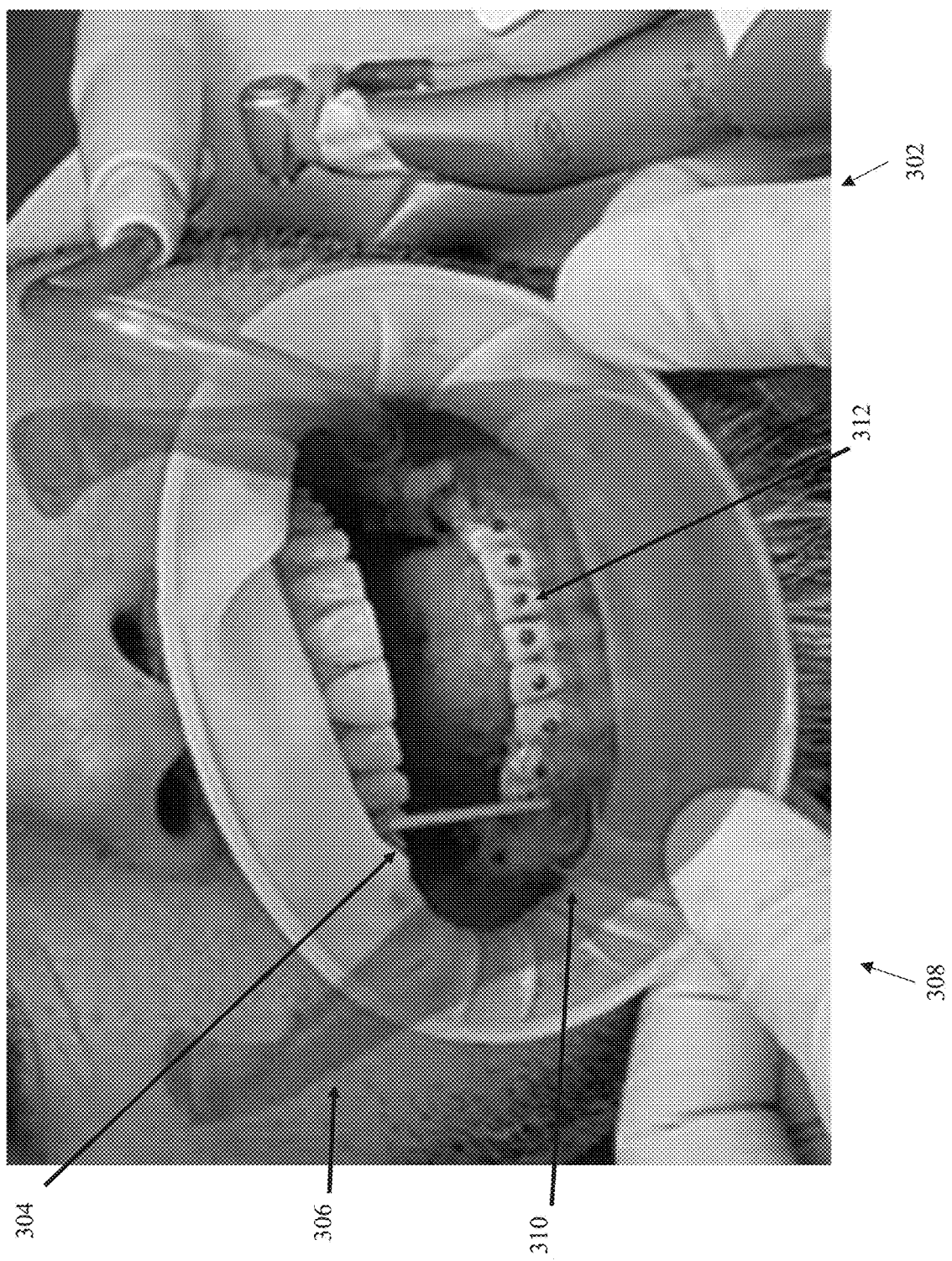
FIG. 3 is a schematic of an exemplary GUI depicting a virtual vector positioned within a dental-related anatomical structure overlaid on a frame, in accordance with some embodiments of the present invention.
Figure 4:
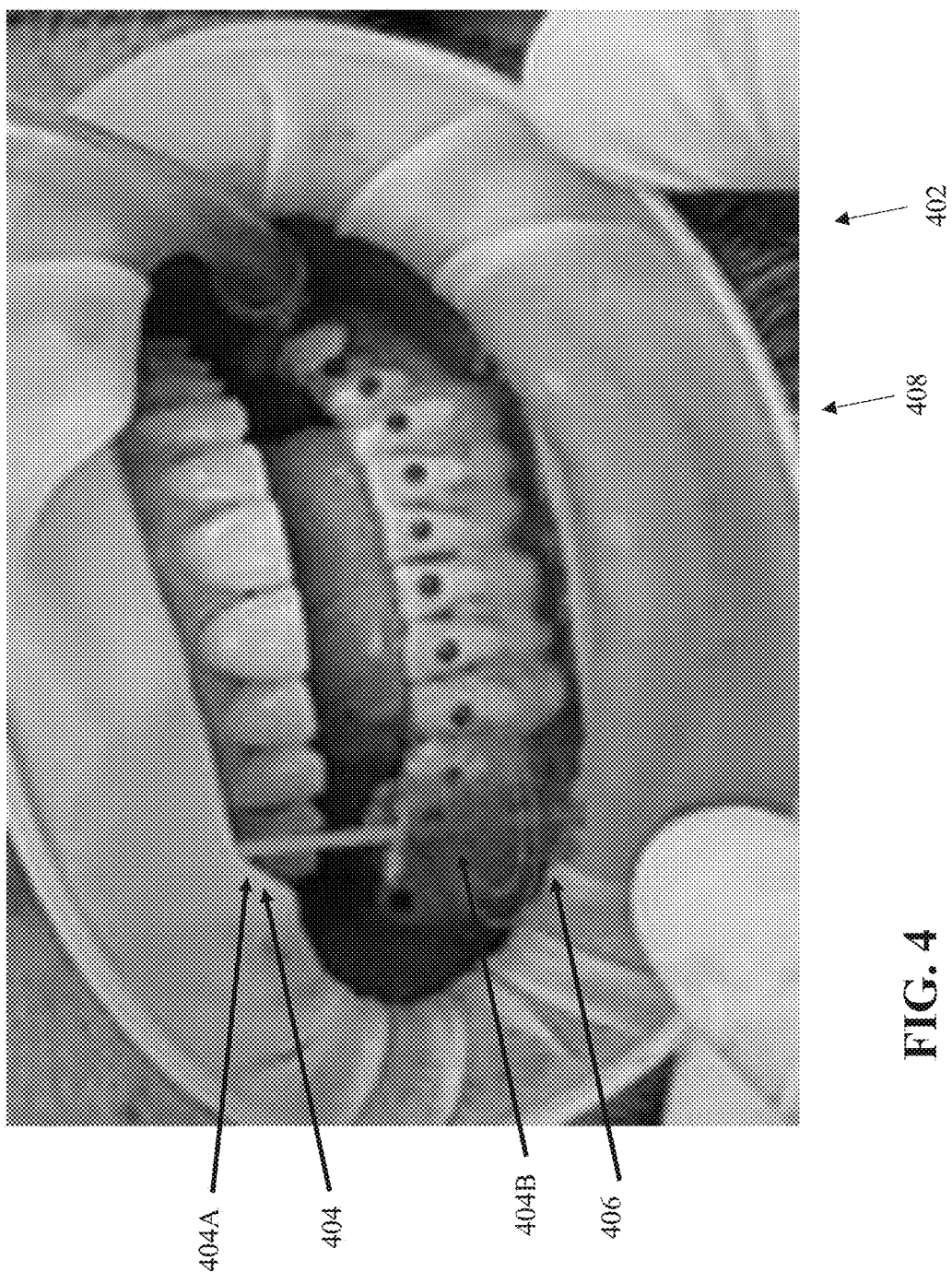
FIG. 4 is a schematic of an exemplary GUI depicting a 3D virtual model of a dental implant positioned with respect to a virtual vector overlaid on a frame, in accordance with some embodiments of the present invention.
Figure 5:
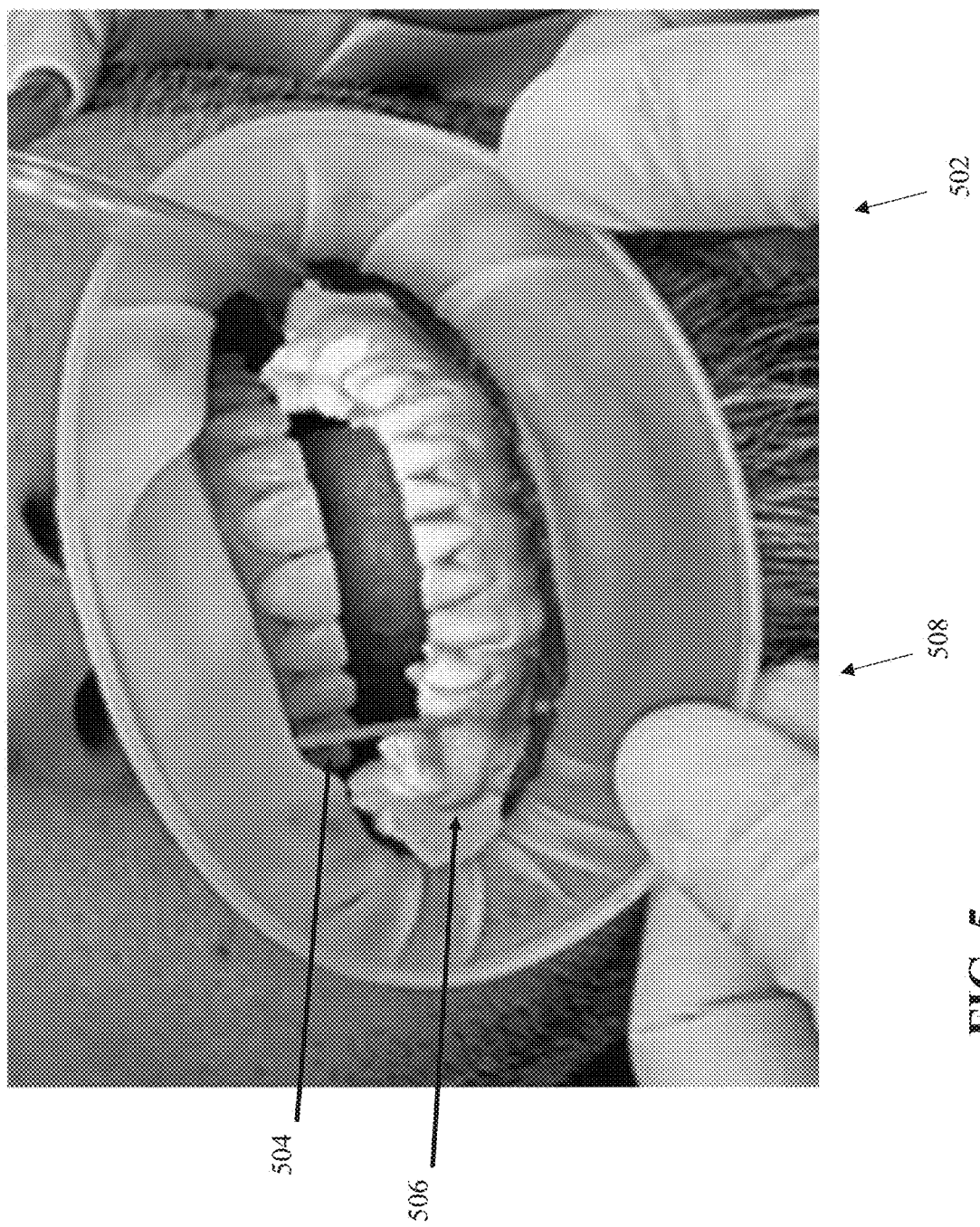
FIG. 5 is a schematic of an exemplary GUI depicting a virtual vector positioned within a dental 3D visual model overlaid on a frame, in accordance with some embodiments of the present invention.
Figure 6:
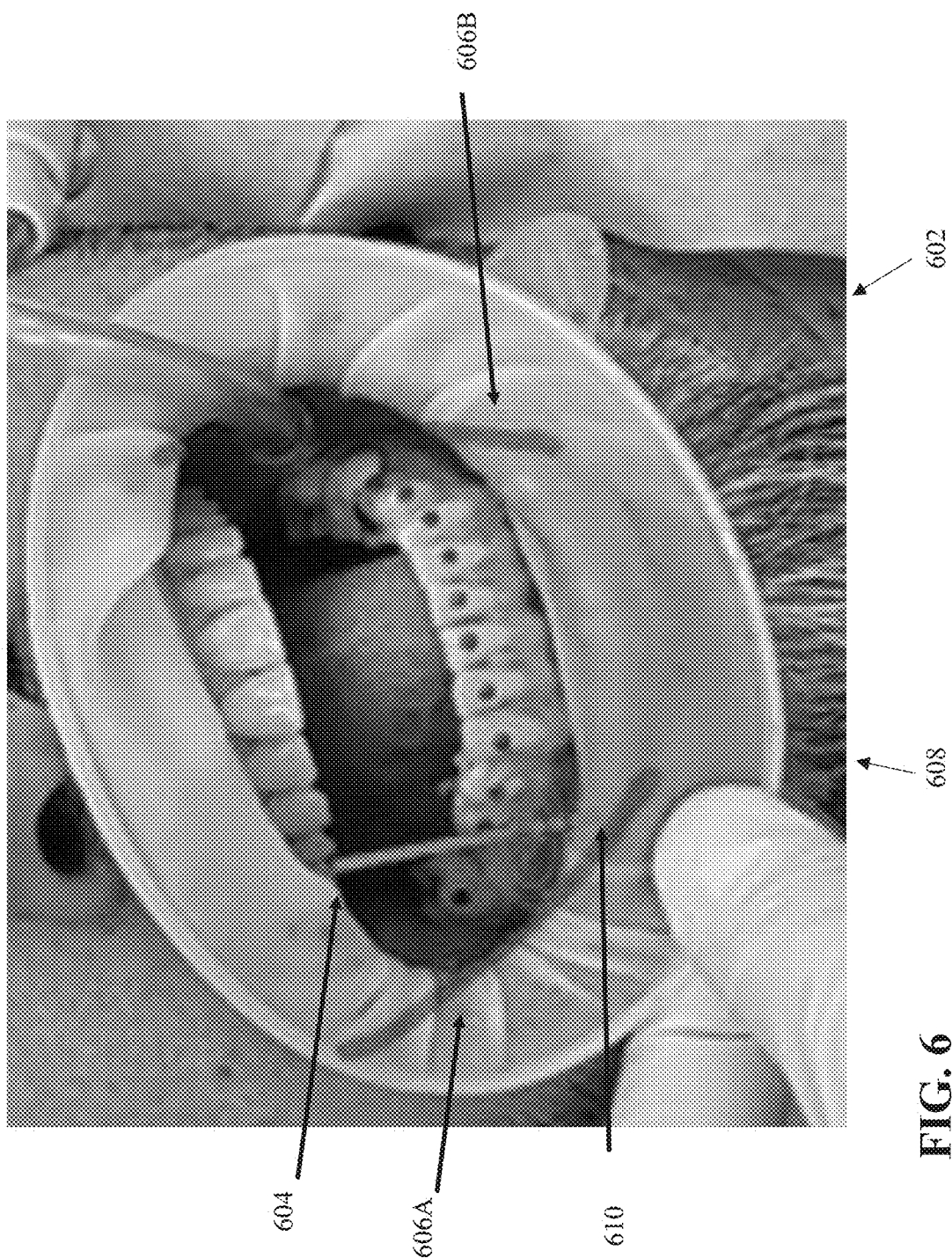
FIG. 6 is a schematic of an exemplary GUI depicting a virtual vector positioned relative to another dental-related anatomical structure overlaid on a frame, in accordance with some embodiments of the present invention.
Figure 7:
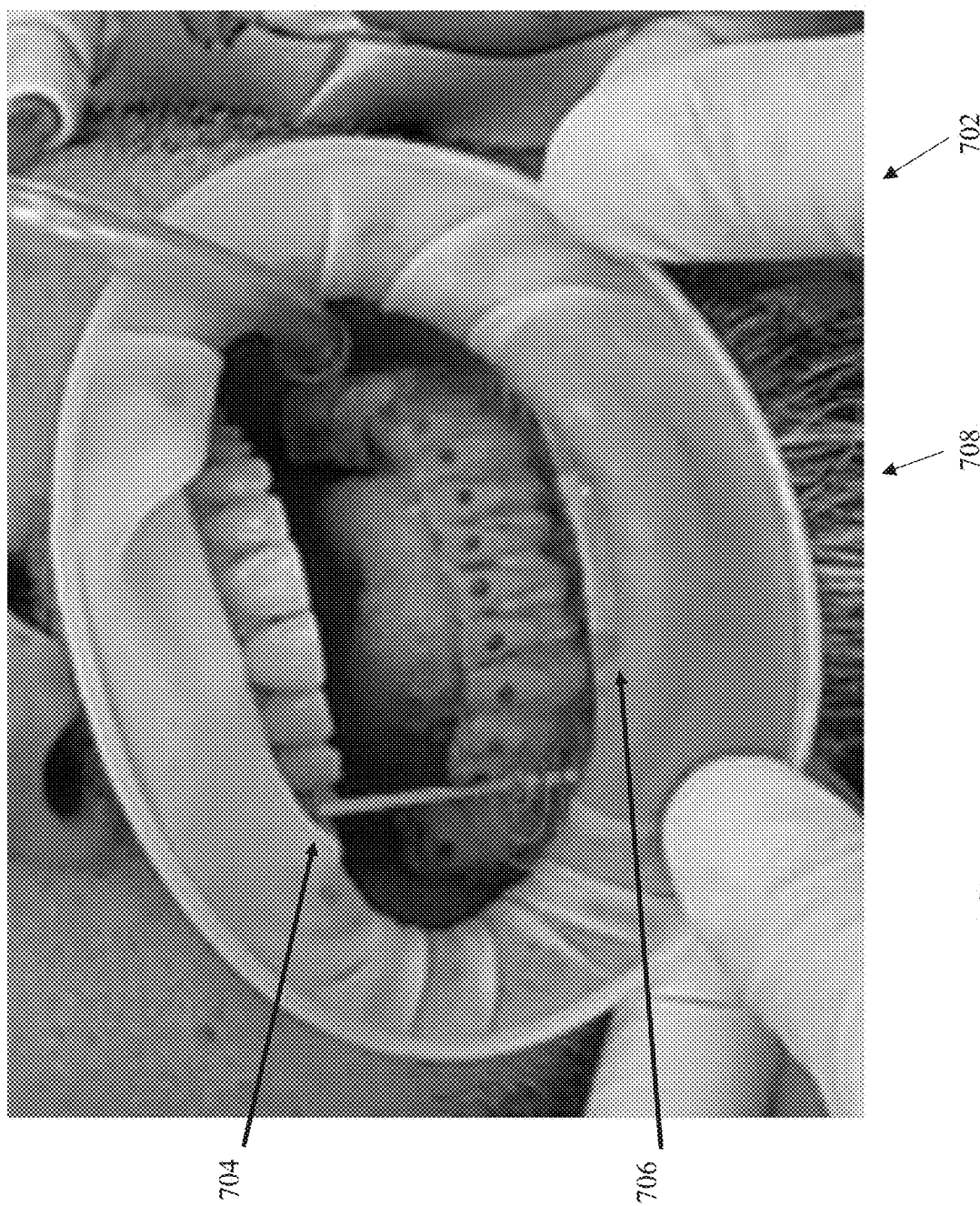
FIG. 7 is a schematic of an exemplary GUI depicting a virtual vector positioned relative to yet another dental-related anatomical structure overlaid on a frame, in accordance with some embodiments of the present invention.

Reference is now made to FIG. 1, which is a block diagram of a system 100 for generating and/or updating a GUI for planning positioning of a dental implant in a subject, in accordance with some embodiments of the present invention. Reference is also made to FIG. 2, which is a flowchart of a method of generating and/or updating a GUI for planning positioning of a dental implant in a subject, in accordance with some embodiments of the present invention. Reference is also made to FIG. 3, which is a schematic of an exemplary GUI 302 depicting a virtual vector 304 positioned within a dental-related anatomical structure 306 overlaid on a frame 308, in accordance with some embodiments of the present invention. Reference is also made to FIG. 4, which is a schematic of an exemplary GUI 402 depicting a 3D virtual model of a dental implant 406 positioned with respect to a virtual vector 404 overlaid on a frame 408, in accordance with some embodiments of the present invention. Reference is also made to FIG. 5, which is a schematic of an exemplary GUI 502 depicting a virtual vector 504 positioned within a dental 3D visual model 506 overlaid on a frame 508, in accordance with some embodiments of the present invention. Reference is also made to FIG. 6, which is a schematic of an exemplary GUI 602 depicting a virtual vector 604 positioned relative to another dental-related anatomical structure 606 overlaid on a frame 608, in accordance with some embodiments of the present invention. Reference is also made to FIG. 7, which is a schematic of an exemplary GUI 702 depicting a virtual vector 704 positioned relative to yet another dental-related anatomical structure 706 overlaid on a frame 708, in accordance with some embodiments of the present invention.

System 100 described with reference to FIG. 1 may implement the features of the method described with reference to FIG. 2, by one or more processors 102 of a computing environment 104 executing code instructions 106A stored on a memory 106.

Computing environment 104 may be implemented as, for example, a client terminal, a server, a virtual machine, a virtual server, a computing cloud, a mobile device, a desktop computer, a thin client, a Smartphone, a Tablet computer, a laptop computer, and an augmented reality device. Computing environment 104 may include an advanced visualization workstation that sometimes is add-on to a dentistry workstation and/or other devices.

Computing environment 104 may receive image(s) captured by image sensor(s) 112, process the images optionally using additional data (e.g., obtained from data storage device 152, repository of data 120A, and/or other sources), and generate a presentation (e.g., fused images and/or overlays) on a user interface 150, optionally an augmented reality presentation, as described herein.

Image sensor(s) 112 may be implemented as cameras capturing images in the visible light spectrum for example, CCD, CMOS sensors, and/or red green blue (RGB) sensor.

User interface(s) 150 may be implemented as an Augmented Reality (AR) display device, for example, a Head Mounted Display (HMD), AR goggles, and/or the like.

Alternatively or additionally, system 100 includes one or more accessory user interfaces 124, which may be in communication with computing environment 104. Accessory user interface(s) 124 may be used by a user, for example, to input data, such as select which internal anatomical structure of the subject to depict in an overlay over a visible light image of the oral cavity of the subject (e.g., nerves, jawbone, roots of teeth), as described herein. For example, accessory user interface(s) 124 may include a microphone and voice activated software to enable the user (e.g., dentist) to issue voice commands, such as for selecting what is presented within the GUI. Accessory user interface(s) 124 may be used, for example, for presenting additional data in addition to, and/or alternatively to, user interface 150. For example, fused images presented within an AR display device may also be presented on a secondary display. In another example, CT scans, oral scans, and the like, which are not presented within the AR display may be presented on the secondary display. Accessory user interface(s) 124 may include, for example, one or more of: a touchscreen, a display screen, a keyboard, a mouse, and voice activated software using speakers and microphone.

Multiple architectures of system 100 based on computing environment 104 may be implemented:

In an exemplary implementation of a localized architecture, computing environment 104 may provide dedicated and/or localized services (e.g., one or more of the acts described with reference to FIG. 2), for example, to a dentist in a clinic. Computing environment 104 may be implemented within user interface 150, for example, within an AR device. In another example, computing environment 104 may be external to user interface 150, and in local communication with user interface 150, optionally over network 110, such as a local network, a wireless communication channel (e.g., short range), cables, and the like. For example, computing environment 104 is implemented as a dental workstation, a laptop, a desktop, and/or a server in a dental clinic. Computing environment 104 may locally obtain images from image sensors 112, generate the fused image(s) and/or overlay (e.g., as described herein), and provide the fused image(s) and/or overlay for presentation on user interface 150.

In an exemplary implementation of a centralized architecture, computing environment 104 may be implemented as one or more servers (e.g., network server, web server, a computing cloud, a virtual server) that provides centralized services (e.g., one or more of the acts described with reference to FIG. 2) to one or more interfaces 150 and/or client terminals 108 and/or servers 118 in communication with user interfaces 150 over a network 110, for example, providing software as a service (SaaS), software services accessible using a software interface (e.g., application programming interface (API), software development kit (SDK)), an application for local download, and/or providing functions using a remote access session, such as through a web browser and/or viewing application. For example, computing environment 104 may be implemented as a server in a dental clinic, providing services to multiple client terminals 108 implemented as dental work stations located in multiple rooms. In each room, a dentist is wearing an AR device (e.g., user interview 150) which is in local communication with a respective dental work station. Images sensors 112 in each room send their images to the server (i.e., 104) over network 110 optionally vial their respective local client terminals 108. Fused images and/or overlays are centrally generated by the server, and sent over the network to respective work stations for local presentation on respective AR devices.

Image sensor(s) 112 may transmit captured images (e.g., of the oral cavity of a dental patient) to computing environment 104, for example, via a direct connected (e.g., local bus and/or cable connection and/or short range wireless connection), and/or via network 110 and a network interface 122 of computing environment 104 (e.g., where sensor(s) 112 are connected via internet of things (IoT) technology and/or are located remotely from the computing environment 104). In another implementation, images captured by sensor(s) 112 are sent to computing environment 104 via client terminal 108 and/or server 118 which may be in local communication with sensor(s) 112.

Network interface 122 may be implemented as, for example, a wire connection (e.g., physical port), a wireless connection (e.g., antenna), a network interface card, a wireless interface to connect to a wireless network, a physical interface for connecting to a cable for network connectivity, and/or virtual interfaces (e.g., software interface, application programming interface (API), software development kit (SDK), virtual network connection, a virtual interface implemented in software, network communication software providing higher layers of network connectivity).

Processor(s) 102 of computing environment 104 may be hardware processors, which may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include a single processor, or multiple processors (homogenous or heterogeneous) arranged for parallel processing, as clusters and/or as one or more multi core processing devices.

Memory 106 stores code instructions 106A executable by hardware processor(s) 102. Exemplary memories 106 include a random access memory (RAM), read-only memory (ROM), a storage device, non-volatile memory, magnetic media, semiconductor memory devices, hard drive, removable storage, and optical media (e.g., DVD, CD-ROM). For example, memory 106 stores code 106A that execute one or more acts of the method described with reference to FIG. 2.

Computing environment 104 may include a data storage device 120 for storing data, for example, a repository of data 120A that may store data as described herein, for example, CT images, 3D models, intraoral scan, and the like. Data storage device 120 may be implemented as, for example, a memory, a local hard-drive, a removable storage unit, an optical disk, a storage device, a virtual memory and/or as a remote server 118 and/or computing cloud (e.g., accessed over network 110).

Alternatively or additionally, computing environment 104 may be in communication (e.g., over a network 110) with one or more data storage devices 152 that may store data used herein, for example, CT images, 3D models, intraoral scan, and the like. Examples of data storage devices 152 include: data storage servers, cloud storage, external data storage devices, and the like.

Referring now back to FIG. 2, at 202, sequential frames of an oral cavity of a subject are accessed.

The frames may be captured by one or more image sensors (e.g., camera) during a dental session of the subject. For example, the frames are captured by a camera which may be located on an AR device worn by a user (e.g., dentist) during the dental session.

The terms frame and image may be used interchangeably.

The frames may be 2D images.

The frames may be presented, optionally within the AR device worn by the user.

The frames serve as a basis within the GUI, where one or more visual elements may be presented as an overlay over the frames, and/or one or more fused frames may be created and presented within the GUI, as described herein.

At 204, a real-world location and/or angle of a real-world tool manipulated by a user is computed. The real-world location and/or angle may be dynamically computed in response to manipulations by the user, for example, displacement in 3D space, and/or change in angle. It is noted that change in rotation is not necessarily computed, based on the assumption that the drill bit rotates for drilling, and determination of rotation is not relevant.

The real-world location and/or angle of the real-world tool may be computed using different approaches. For example, in one approach, outputs of one or more pose sensors installed on the tool is analyzed to obtain the pose of the tool. In another example, predefined features of the real-world tool are extracted from the 2D frame. The predefined features may be matched to corresponding predefined features of a 3D model of the tool which may be set a baseline pose, such as aligned along one or more axes. The location and/or angle of the tool may be computed based on a translation from the predefined features extracted from the 2D frame to the predefined features of the 3D model. In yet another example, one or more predefined markers having a known baseline pose are connected to the tool. The predefine markers are detected on the 2D frame. The location and/or angle of the tool may be computed based on a translation from the pose of the markers extracted from the 2D frame to the known baseline pose.

The real world location of the jaw and/or other anatomical structures may be computed. The real world location of the jaw and/or other anatomical structures may be computed based on a detection of the teeth in the image (e.g., by a detector model, a segmentation model, and/or by detecting intraoral markers placed on the teeth), and registering the teeth to a dental 3D imaging model of the teeth (e.g., acquired from the 3D image, such as a CT scan). The registration may be performed, for example, based on a simultaneous localization and mapping (SLAM) approach by solving the estimation of the pose of the camera on the AR device, and obtaining a MVP (model-view-projection) matrix which translates the location of the model (e.g., jaw) to the camera space. An analogous may be computed for the drill, which may be detected (e.g., by a detector model, a segmentation model, and/or by detecting one or more features and/or markers), registering the drill with a corresponding 3D model (e.g., acquired by 3D scanning the drill during a pre-procedure calibrations process) and solving its MVP model view projection matrix with SLAM. The outcome of having each model (e.g., jaw, drill) at each frame and a corresponding updated model view matrix for each model, selected locations may be projected from a certain coordinate space of each of the model to the common camera coordinate space (e.g., denoting the real world). Distances may be measured within the common camera coordinate space, for example, the distance from the tip of the bur of the drill to the nerve.

It is noted that the real-world location is optional, since other data for implementing features described herein may be extracted and/or computed based on the coordinate space of the camera (e.g., corresponding to the real world). The AR device's spatial awareness feature may be used to track the location and/or movement of the camera in the real world in order to remove estimated movement that may be a possible solutions in the SLAM but do not correlate with the boundaries of the spatial awareness of the AR device and as a result get better more optimal SLAM performance.

The real-world tool may be implemented as a drill used by a dentist for drilling into the jaw, for inserting a dental implant. The location may be defined according to a tip of a bur of the drill. The angle may be defined between the bur of the drill and a plane parallel to an x-y plane of a coordinate system of the frames, at a pivot point defined by the tip of the bur.

The real-world location and/or angle may be computed within the coordinate system of the frames. Optionally, the frames are registered to the coordinate system, and the real-world location and/or angle of the tool is computed relative to the coordinate system. The frames may be registered to the coordinate system by defining the coordinate system relative to a dental 3D imaging model of the subject that includes anatomical features relates to the oral cavity, for example, a CT scan and/or MRI scan. The coordinate system may represent real-world measurements based on the dental 3D imaging model. The location and/or angle of the tool may be defined within the coordinate system defined based on the dental 3D imaging model.

At 220, the GUI may be dynamically updated based on one or more features described with reference to 202-218.

For clarity and simplicity of explanation, the update of the GUI is initially described with reference to 204. Additional possible updates of the GUI are described with reference to other features below.

The GUI may be dynamically updated according to the computed real-world location and/or angle of the tool. The real-world location and/or angle of the tool correspond to a virtual location and/or virtual angle defining a virtual vector. The virtual vector may be defined as directly corresponding to the real-world location and/or angle of the tool. Alternatively, the virtual vector may be defined at an offset of the virtual location relative to the real-world location of the real-world tool. For example, the virtual vector is displaced 2 cm to the left of the real-world location of the tool along the x-axis of the coordinate system.

The virtual vector may be presented as an overlay overlaid on the sequential frames, where the virtual location and/or virtual angle are dynamically updated, corresponding to the real-world location and/or angle of the real-world tool which may be dynamically adapted by manipulations of the use.

The virtual vector depicted in the GUI may be dynamically updated according to dynamic manipulations of the tool by the user, enabling the user to select a desired location and/or angle, such as for drilling into the jaw of the subject for insertion of a dental implant.

At 222, one of more features described with reference to 202-220 may be iterated. During iterations, different features may be implemented, as described herein. The features are now described, without necessarily being limited to a specific sequence and/or order. The numbering of the blocks 202-220 representing features, are for convenience only, without defining a specific sequence and/or order. Different sequences and/or arrangements may be implemented.

Different exemplary flows are now described. The flows are not necessarily limiting, and may be in different sequences and/or orders. The flows may represent an iteration. After each flow, the GUI may be updated accordingly, as described with reference to 220. Another iteration may follow, as described with reference to 222. During each iteration, visual features described with respect to different flows may be added for presentation within the GUI or removed from the GUI (when previously presented), for example, during a first iteration dental-related anatomical structure (e.g., as described with reference to 208) is depicted, during a second iteration a 3D virtual model of a dental implant (e.g., as described with reference to 212) is depicted simultaneously with the dental-related anatomical structure, and during a third flow a dental 3D visual model (e.g., as described with reference to 216) is depicted simultaneously with the dental-related anatomical structure and with the 3D virtual model.

In one exemplary flow, feature 218 is implemented during an iteration.

At 218, the virtual location and/or virtual angle of the virtual vector may be fixed with respect to the subject. The virtual vector may be fixed with respect to the coordinate system described herein, such that upon changes to the pose of the camera capturing the frames (e.g., as described with reference to 202), the GUI is updated by updating the overlay for indicating the virtual vector at the same fixed location and/or angle.

Once the virtual location and/or virtual angle of the virtual vector is fixed, the fixed virtual location and/or fixed virtual angle is independent of the real-world location and/or angle of the real-world tool.

The fixing may be set in response to an input from the user, which may be received via the GUI and/or another device. For example, the user may say a defined phrase into a microphone to indicate the fixing, for example, "fix it". In another example, the user or an assistant may press an icon on the GUI presented on a display.

Optionally, the fixing is done in two steps. In a first step, the location of the virtual vector is fixed. Once the location is fixed, the angle of the virtual vector may be adapted while retaining its fixed location according to manipulations of the tool. The angle is then fixed with respect to the fixed location of the virtual vector.

Optionally, a 3D virtual model of a dental implant, for example as described with reference to 212 and/or 214, is depicted at a location and angle corresponding to the fixed location and angle. Alternatively, first the 3D virtual model of the dental implant is generated and/or adapted, and then the 3D virtual model of the dental implant is fixed.

Optionally, in subsequent iterations following the fixing of the 3D virtual model of a first dental implant, the virtual angle and/or virtual location of a simultaneously presented second virtual vector, is fixed. The second virtual vector may be for planning insertion of a second dental implant with respect to the 3D virtual model of the first dental implant. The procedure for insertion of two dental implants, which may be positioned side by side, may be planned. Insertion of additional dental implants may be planned accordingly.

A fixed virtual vector may be released (e.g., in response to an input by a user) and re-fixed at a different location and/or angle.

Once the virtual vector has been fixed (e.g., the user is pleased with the location and/or angle), the fixed virtual vector may be used for guiding the drilling procedure. The GUI may be updated accordingly. An exemplary approach for updating the GUI for guiding the drilling procedure based on the fixed virtual vector is described, for example, with reference to co-filed U.S. Patent Application entitled "INTERACTIVE GUIDANCE OF DENTAL IMPLANT SURGERY" U.S. patent application Ser. No. 18/656,634, filed on May 7, 2024, the contents of which are incorporated herein by reference in their entirety.

Another exemplary flow based on features 206-210 is now described. It is to be understood that one or more features described with reference to 218-222 may be implemented following the described flow.

At 206, one or more dental-related anatomical structures of the subject may be selected, optionally by the user.

The dental-related anatomical structures may be selected using an input mechanism, for example, by analyzing speech of the user (e.g., the user saying "display jawbone", or "show me the nerves"), pressing an icon on a screen, manipulating another tool, and the like.

The dental-related anatomical structure(s) may include an internal anatomical structure located, such as below an intraoral surface of the subject. Examples of dental-related anatomical structures include roots of teeth, jawbone, and one or more nerves. The dental-related anatomical structure(s) may be significant for drilling and/or insertion of the implant. For example, the dental-related anatomical structures may represent anatomical structures which are to be avoided during drilling such as nerves, and/or may represent structures to be drilling into such as the jawbone.

The dental-related anatomical structure may be segmented from the dental 3D imaging model which may be registered to the sequential frames. The dental 3D imaging model may be created based on a 3D scan of the oral cavity of the subject, which may be captured pre-procedure, for example, a CT scan and/or MRI scan. One or more dental-related anatomical structures may be identified within the 3D scan, for example, automatically by one or more detector models and/or manually by a user.

At 208, the selected dental-related anatomical structure(s) may be presented within the GUI presenting the images of the oral cavity (e.g., captured by the camera).

The dental-related anatomical structure(s) may be registered to the images of the oral cavity, and presented according to the registration, such as within a common coordinate system.

Optionally, the dental-related anatomical structures are presented within the GUI in one or more fused frames. The fused frames represent a merger of the sequential frames and a segmentation of the dental-related anatomical structure of the subject.

The fused frames may be created as follows: The frame may be registered to the dental 3D imaging model. The registration may be performed by aligning features of the frame with corresponding features of the dental 3D imaging model. The features used for alignment may be, for example, special markers placed on teeth of the user that are present during the 3D scan used to create the dental 3D imaging model, and during the dental procedure while the frames are being captured. In another example, the features for alignment may be a segmentation of teeth. A segmentation of the dental-related anatomical structure segmented from the dental 3D imaging model may be accessed. The fused frame may be created by merging the frame with the segmentation of the dental-related anatomical structure, while maintain the registration between the frame and the dental 3D imaging model.

Additional details of exemplary approaches for creating fused frames are described, for example, with reference to International Patent Application Publication No. WO2022/190105, entitled "ENHANCING DENTAL VIDEO TO CT MODEL REGISTRATION AND AUGMENTED REALITY AIDED DENTAL TREATMENT", filed on Mar. 10, 2022, and assigned to the same Assignee as the present application, the contents of which are incorporated herein by reference in its entirety.

The overlay of the virtual vector may be presented over each fused frame. The virtual vector may be depicted with respect to the segmentation of the dental-related anatomical structure(s) presented in the fused frame. When the virtual vector is positioned at least partially below a surface of the oral cavity, such as at least partially within tissues of the jaw, the virtual vector may be visually depicted at least partially penetrating the tissue. For example, different intensity of pixels and/or different patterns may be used for of portions of the virtual vector located "outside" tissues and for portions of the virtual vector located "inside" tissues. This may enable the user to visualize the drilling route from outside the tissues, inside tissues, and in relation to the internal dental-related anatomical structures.

At 210, a distance between the virtual vector and one or more of the dental-related anatomical structures may be computed. The distance may be dynamically computed in response to adaptation of the virtual vector in response to manipulations of the tool by the user.

An indication (e.g., alert) may be generated according to the distance. Optionally, the indication is generated when the distance is below a threshold indicating risk to the nearby dental-related anatomical structure. For example, when the virtual vector is too close to the nerve. Alternatively or additionally, the indication is generated when the distance is above a threshold indicating a safe margin from the nearby dental-related anatomical structure. For example, when the virtual vector is a safe distance away from the nerve. The indication may be, for example, a message, a change in color of the virtual vector, a pop-up visual element presented on the GUI, and the like.

With respect to feature 220, the GUI may be dynamically updated for presenting one or more of: the fused frames depicting the dental-related anatomical structure(s), the virtual vector within the fused frame and with respect to the dental-related anatomical structure(s), a presentation of the distance, and the generated indication of indicating whether the virtual vector is within a safe margin and/or poses a risk according to the distance.

Another exemplary flow based on features 212-214 is now described. It is to be understood that one or more features described with reference to 218-222 may be implemented following the described flow.

At 212, another overlay (which may be included in the current overlay and/or as a separate overlay) of a 3D virtual model of a dental implant for implantation along the virtual vector may be generated.

The 3D virtual model of the dental implant may be positioned at the virtual location of the virtual vector, at an angle defined by the virtual angle.

The 3D virtual model is presented within the GUI, over the sequential frames that may include the virtual vector. The 3D virtual model may be presented within the GUI simultaneously with other depicted visual features, for example, the dental-related anatomical structure(s) described herein and/or the dental 3D visual model described herein.

The 3D virtual model of the dental implant may represent the implant portion that is inserted into the teeth and/or the dental prosthesis that connects to the implant, such as the crown.

The 3D virtual model of the dental implant positioned along the virtual vector, as depicted in the GUI, may be dynamically updated according to the corresponding physical angle and/or physical location of the tool manipulated by the user.

At 214, the 3D virtual model of the dental implant may be dynamically adapted.

One or more parameters of the 3D virtual model of the dental implant may be dynamically adapted.

Examples of parameters that may be adapted include size (e.g., length and/or diameter and/or width and/or height), shape, and/or type (e.g., manufacturer, model).

The adaption may be in response to input from a user, for example, selection via voice activation, manipulation of a tool, and/or by selection of an icon on a display. Alternatively, the adaptation may be automatic, for example, a code (e.g., process, machine learning model) may automatically select parameters of the dental implant according to the location of the virtual vector and/or according to other nearby teeth. For example, the size of the dental implant is selected according to the location of the nerve, and the type of the dental implant is selected to look like the tooth that is being replaced.

Another exemplary flow based on feature 216 is now described. It is to be understood that one or more features described with reference to 218-222 may be implemented following the described flow.

At 216, a dental 3D visual model of the subject may be depicted within the GUI, optionally as an overlay over the subject's teeth and/or jaw. The dental 3D visual model may be created by an intraoral scanner capturing images at the visual light spectrum.

The user may select to include or exclude the dental 3D visual model, for example, by voice activation, using a tool, and/or selecting an icon on a display.

The virtual vector may be presented with respect to the dental 3D visual model. When the virtual vector is positioned at least partially below a surface of the dental 3D visual model, the virtual vector may be visually depicted at least partially penetrating the dental 3D visual model. For example, different intensity of pixels and/or different patterns may be used for of portions of the virtual vector located "outside" the dental 3D visual model and for portions of the virtual vector located "inside" the dental 3D visual model. This may enable the user to visualize the drilling route from outside the tissues, inside tissues, and in relation to anatomical structures of the dental 3D visual model.

The location and/or angle of the virtual vector with respect to the dental 3D visual model may be dynamically updated in response to manipulations of the tool by the user.

The dental 3D visual model may be presented as a second overlay on the sequential frames, and/or as part of the current overlay.

The dental 3D visual model may be presented within the GUI according to a registration between the dental 3D visual model, the dental 3D imaging model, and the sequential frames. The virtual vector may be overlaid on the dental 3D visual model and the sequential frames according to a corresponding physical angle and/or physical location of the tool manipulated by the user.

The dental 3D visual model may be presented within the GUI using the following exemplary approach. The dental 3D visual model may be registered to the dental 3D imaging model described herein (e.g., generated based on a pre-procedure 3D image such as a CT and/or MRI scan). The registration may be done, for example, matching intraoral markers located on teeth of the subject depicted in the dental 3D visual model to intraoral markers in the dental 3D imaging model, and/or by matching a teeth segmented from the dental 3D visual model to the same corresponding teeth segmented from the dental 3D imaging model. The frame may be registered to the dental 3D visual model according to the intraoral markers and/or according to the teeth segmented from the 2D frame. The frame may be registered to the dental 3D imaging model according to the registration of the frame to the dental 3D visual model, and/or according to the registration of the dental 3D visual model to the dental 3D imaging model. A fused frame (which may be another fused frame different than the fused frame described with reference to 208, or in addition to the fused frame described with reference to 208) may be created by merging the frame with a corresponding portion of the registered dental 3D visual model. A second overlay (which may be different than the current overlay, or part of the current overlay) of the virtual angle and/or the virtual location of the virtual vector on the fused frame may be adapted according to a corresponding physical angle and/or physical location of the tool manipulated by the user.

Referring now back to FIG. 3, GUI 302 depicts virtual vector 304 overlaid on frame 308 depicting a mouth of a subject captured by a camera. GUI 302 may be presented within an AR device worn as a headset by a user, optionally a dentist, for planning insertion of a dental implant according to virtual vector 304, as described herein.

GUI 302 further depicts a jawbone (i.e., dental-related anatomical structure) 306.

Virtual vector 304 is positioned relative to jawbone 306, for indicating the location and/or angle where the dental implant is to be positioned.

Jawbone 306 may be registered to frame 308 based on markers 312 placed on the teeth of the subject, and/or segmentation of the teeth of the subject, as described herein.

One or more visual markers 310 may be presented with respect to virtual vector 304, for example, concentric circles. A tip of virtual vector 304 may be positioned within a center of concentric circles 310. Virtual vector 304 may represent a normal of a plane of concentric circles 310. Concentric circles 310 may help visualize the location and/or angle of virtual vector 304.

GUI 402 depicts the 3D virtual model of dental implant 406 positioned with respect to virtual vector 404 overlaid on a frame 408 depicting a mouth of a subject captured by a camera. A top portion 404A of virtual vector 404 depicted as external to dental implant 406 is shown with pixels of a higher intensity. A bottom portion 404B of virtual vector 404 depicted as internal to dental implant 406 is shown with pixels of a lower intensity.

Referring now back to FIG. 5, GUI 502 depicts virtual vector 504 positioned within dental 3D visual model 506 overlaid on frame 508 depicting a mouth of a subject captured by a camera. Dental 3D visual model 506 may be registered to frame 508 as described herein.

Referring now back to FIG. 6, GUI 602 depicts virtual vector 604 positioned relative to nerves 606A and 606B (i.e., another dental-related anatomical structure) overlaid on frame 608. GUI 602 may depict where a tip 610 of virtual vector 604 is relative to nerve 606A, for example, whether tip 610 is too close to nerve 606A, whether tip 610 penetrates nerve 606A, whether tip 610 is a safe distance away from nerve 606A, and the like.

Referring now back to FIG. 7, GUI 702 depicts virtual vector 704 positioned relative to teeth roots 706 (i.e., the yet another dental-related anatomical structure) overlaid on frame 708. GUI 602 may depict where virtual vector 704 is relative to teeth roots 706, for example, whether too close, or a safe distance away.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant GUIs will be developed and the scope of the term GUI is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method for processing data using at least one processor coupled to a memory, the method comprising:
   presenting, within the GUI, sequential frames of an oral cavity of a subject captured by at least one image sensor during a dental session of the subject;
   computing a real-world location and/or angle of a real-world tool manipulated by a user; and
   dynamically updating, within the GUI, an overlay of a virtual angle and/or virtual location of a virtual vector overlaid on the sequential frames corresponding to the real-world location and/or angle of the real-world tool,
   wherein the virtual vector denotes a location and angle for drilling by a bur of a drill for implanting the dental implant.

2. The computer-implemented method of claim 1, wherein the GUI including the sequential frames and overlay are presented within an augmented reality device.

3. The computer-implemented method of claim 1, wherein the real-world tool comprises the drill for inserting the dental implant.

4. The computer-implemented method of claim 1, wherein the virtual angle and/or virtual location of the virtual vector is offset from the real-world location of the real-world tool being manipulated for dynamically updating the virtual vector.

5. The computer-implemented method of claim 1, further comprising:
   receiving a selection of at least one dental-related anatomical structure of the subject;

presenting within the GUI, at least one fused frame depicting a merger of the sequential frames and a segmentation of the at least one dental-related anatomical structure of the subject segmented from a dental 3D imaging model registered to the sequential frames, wherein the overlay of the virtual vector is overlaid on the at least one fused frame, and the virtual vector is depicted with respect to the segmentation of the at least one dental-related anatomical structure.

6. The computer-implemented method of claim 5, wherein the at least one dental-related anatomical structure comprises an internal anatomical structure located below an intraoral surface of the subject.

7. The computer-implemented method of claim 5, further comprising dynamically updating within the GUI, the virtual vector depicted at least partially penetrating the segmentation of the at least one dental-related anatomical structure according to manipulations of the tool by the user.

8. The computer-implemented method of claim 5, further comprising dynamically updating within the GUI, a presentation of distance between the virtual vector and the at least one dental-related anatomical structure.

9. The computer-implemented method of claim 8, further comprising generating an indication within the GUI, indicating whether the virtual vector is within a safe margin and/or poses a risk, according to the distance.

10. The computer-implemented method of claim 5, wherein the at least one dental-related anatomical structure is selected from: roots of teeth, jawbone, and at least one nerve.

11. The computer-implemented method of claim 1, further comprising dynamically adapting within the GUI, a second overlay over the sequential frames of a virtual angle and/or virtual location of a 3D virtual model of a dental implant for implantation along the virtual vector, according to the corresponding physical angle and/or physical location of the tool manipulated by the use.

12. The computer-implemented method of claim 11, further comprising in response to an input from a user, dynamically adapting a size and/or shape and/or type of the dental implant and/or of a dental prosthesis designed to connect to the dental implant.

13. The computer-implemented method of claim 1, further comprising presenting within the GUI, a dental 3D visual model of the subject created based on a visible light spectrum intraoral scan of the subject, the dental 3D visual model presented as a second overlay on the sequential frames according to a registration between the dental 3D visual model, a dental 3D imaging model, and the sequential frames, wherein the virtual vector is overlaid on the dental 3D visual model and the sequential frames according to a corresponding physical angle and/or physical location of the tool manipulated by the user.

14. The computer-implemented method of claim 13, wherein the dental 3D visual model is created by an intraoral scanner capturing images at the visual light spectrum.

15. The computer-implemented method of claim 13, further comprising dynamically updating within the GUI, the virtual vector depicted at least partially penetrating the dental 3D visual model, according to manipulations of the tool by the user.

16. The computer-implemented method of claim 1, further comprising:
in response to an input from a user, fixing a location and/or an angle of the virtual vector with respect to the subject, and dynamically updating within the GUI, the overlay indicating the fixed location and/or angle of the virtual vector on subsequent frames, wherein the fixed location and/or angle is independent of the real-world location and/or angle of the real-world tool.

17. The computer-implemented method of claim 16, wherein fixing comprises fixing the location of the virtual vector while dynamically updating the angle of the virtual location according to manipulations of the tool, and fixing the angle with respect to the fixed location of the virtual vector.

18. The computer-implemented method of claim 16, further comprising:
presenting within the GUI, a 3D virtual model of the dental implant at a location and angle corresponding to the fixed location and angle.

19. The computer-implemented method of claim 18, further comprising, within the GUI, dynamically adapting the virtual angle and/or virtual location of a second virtual vector presented simultaneously with the positioned 3D virtual model of the dental implant, for planning insertion of a second dental implant with respect to the 3d virtual model of the dental implant.

20. A system for presenting an interactive graphical user interface (GUI) for planning positioning of a dental implant in a subject, comprising:
at least one processor executing a code for:
presenting, within the GUI, sequential frames of an oral cavity of a subject captured by at least one image sensor during a dental session of the subject;
computing a real-world location and/or angle of a real-world tool manipulated by a user; and
dynamically updating, within the GUI, an overlay of a virtual angle and/or virtual location of a virtual vector overlaid on the sequential frames corresponding to the real-world location and/or angle of the real-world tool,
wherein the virtual vector denotes a location and angle for drilling by a bur of a drill for implanting the dental implant.

21. A computer implemented method of generating an interactive user interface for planning positioning of a dental implant in a subject, comprising:
receiving a selection of at least one dental-related anatomical structure of the subject;
receiving at least one frame of an oral cavity of a subject captured by at least one image sensor during a dental session of the subject;
registering the at least one frame to a dental 3D imaging model;
accessing a segmentation of the at least one dental-related anatomical structure segmented from the dental 3D imaging model;
creating at least one fused frame merging the at least one frame with the segmentation of the at least one dental-related anatomical structure; and
dynamically adapting an overlay of a virtual angle and/or a virtual location of a virtual vector overlaid on the at least one fused frame according to a corresponding real-world location and/or angle of a real-world tool manipulated by a user.

22. The computer implemented method of claim 21, further comprising:
receiving a dental 3D visual model of the subject created based on a visible light spectrum intraoral scan of the subject;
registering the dental 3D visual model to the dental 3D imaging model;

registering the at least one frame to the dental 3D visual model according to at least one intraoral marker;

registering the at least one frame to the dental 3D imaging model according to the registration of the at least one frame to the dental 3D visual model and the registration of the dental 3D visual model to the dental 3D imaging model;

creating at least one second fused frame by merging the at least one frame with a corresponding portion of the registered dental 3D visual model; and dynamically adapting a second overlay of the virtual angle and/or the virtual location of the virtual vector overlaid on the at least one second fused frame according to a corresponding physical angle and/or physical location of the tool manipulated by the user.

* * * * *